United States Patent [19]

van Duyn

[11] Patent Number: Plant 6,609

[45] Date of Patent: Feb. 14, 1989

[54] ALSTROEMERIA NAMED EVENING GLOW

[75] Inventor: Cornelis van Duyn, NA Rijnsburg, Netherlands

[73] Assignee: Groot Associates II, Irvine, Calif.

[21] Appl. No.: 57,236

[22] Filed: Jun. 1, 1987

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Jackson & Jones

[57] ABSTRACT

A new Alstroemeria variety characterized by the brightly colored blossoms, the petals of which are bright purple with a yellow striped heart. The plant is early in flowering.

1 Drawing Sheet

BACKGROUND OF THE NEW PLANT

This new Alstroemeria originated as a seedling selected from individual members of breeding stock maintained at Rijnsburg, Holland. The particular seedling was selected by me in 1981 for propagation and testing because of its blossoms produced on upright stems. Specifically, the inner petals are purplish pink with yellow striped hearts on white background (central). The outer petals are solid in purplish pink coloring. The inner petals have well defined longitudinal streaks or flecks of dark purple while the outer petals are limited to a solid purplish pink coloring with fine striped margins. The selected plant was propagated by me at Rijnsburg, Holland through several generations of root divisions to establish that its distinctive characteristics hold true from generation to generation and appear to be firmly fixed.

Breeding efforts commenced in 1978 and propagation is currently being carried out at Rinjsburg, Holland. The nearest variety is the Alstroemeria called Westland and my new variety, Evening Glow, differs from the Westland in that (1) the flowers are smaller (2) the plant is earlier flowering and more productive and (3) the petals are of a lighter shade of purplish pink.

DESCRIPTION OF THE DRAWING

This new variety of the Alstroemeria plant is illustrated by the accompanying photograph which shows a blooming umbel of the plant with buds and flowers in various stages of opening.

DESCRIPTION OF THE NEW PLANT

The following is a detailed description of my new Alstroemeria plant with color designations according to The National Bureau of Standards, Standard Reference Material, No. 2107, comprising the ISCC-NBS Centroid Color Charts and NBS Special Publication, No. 440.

THE PLANT

Origin: Seedling.
Parentage: Seed parent.
Classification: Alstroemeria Hybrid.
Form: A generally erect bush having an upright stalk with flower-bearing branches in simple umbel arrangement at its top.
Height: About 1.45 meters.

Growth: Upright and normal.
Root stock: Tuberous.
Foliage:
- *Quantity.*—Normal.
- *Number of leaves.*—About 12–15 per stem.
- *Size of leaf.*—About 12.5×4.5 cm.
- *Shape of leaf.*—Parallel venation.
- *Texture.*—Smooth.
- *Color.*—Upper side: Dark green. Under side: Dark green.

THE BUD

Form: Long, globular.
Size: Medium.
- *Diameter.*—About 1.2 cm.
- *Length.*—About 3.8 cm.

Peduncle:
- *Length.*—About 15 cm.
- *Texture.*—Smooth.
- *Form.*—Erect.

THE FLOWER

Blooming habit: Profusely during early season in Spring.
Flower size: Medium.
- *Diameter.*—About 6.5 cm.
- *Depth.*—About 4.5 cm.

Borne: Terminal clusters.
Shape: Generally cup shaped with petal tips curling outwardly.
Petalage:
- *Number of petals.*—Six.
- *Arrangement.*—Two concentric circles of three.
- *Form.*—Broad ovate.
- *Texture.*—Soft.
- *Appearance.*—Velvety.

Color:
- *Outer petals.*—Moderate purplish red (No. 258) with fine striped margins of vivid purplish red (No. 254).
- *Inner Petals.*—Moderate purplish red (No. 258) with white (No. 263) center and vivid yellow (No. 82) heart. The inner petals have numerous generally longitudinal stripes or flecks of vivid deep purpish red (No. 257).

Persistence: The flowers hang on and dry.
Main stem or stalk:
- *Length.*—About 15 cm.
- *Color.*—Green.

*Character.*—Strong and upright.

Lasting quality of flower: About 3 weeks. As a cut flower, about 10–14 days.

REPRODUCTIVE ORGANS

Stamens:

*Number.*—Six.

*Arrangement.*—One opposite each petal.

Anthers:

*Size.*—About 0.8 cm×0.2 cm.

*Color.*—Reddish purple (No. 245).

Filaments:

*Length.*—About 3.5 cm.

*Color.*—Light purplish pink (No. 249).

*Pollen.*—Grey.

Pistils:

*Number.*—One.

*Styles.*—Length: About 2–3 cm. Color: Purplish pink.

Fruit:

*Shape.*—Round.

*Color.*—Light brown.

This plant is particularly noted for the distinctive coloration of its flowers, which coloration does not clearly resemble that of any other Alstroemeria plant previously known to me. The vivid deep purplish red flecks on the moderate purplish red inner petals with vivid yellow striped hearts on a white background (central) and outer petals with the moderte purplish red coloring with fine striped margins make this plant an attractive addition to the Alstroemeria family.

I claim:

1. A new and distinctive Alstroemeria cultivar, substantially as herein shown and described, characterized by the distinctive coloration of its medium and profusely blooming flowers.

* * * * *

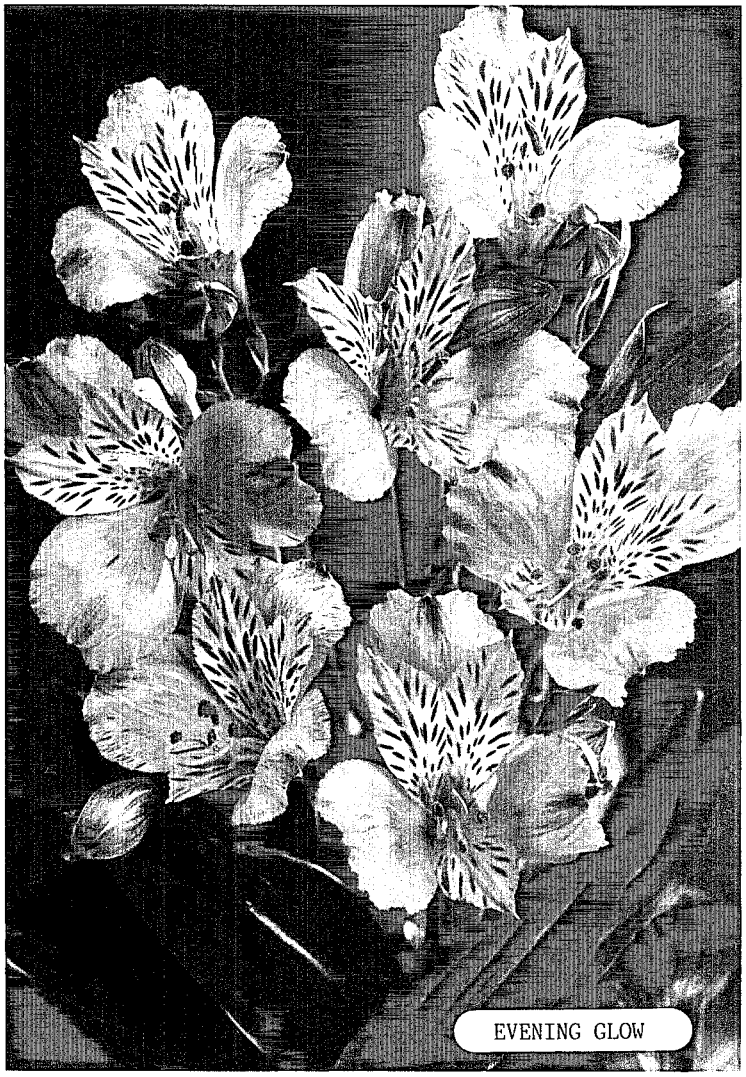
EVENING GLOW